United States Patent
Kraner et al.

(10) Patent No.: US 11,827,718 B2
(45) Date of Patent: Nov. 28, 2023

(54) ANTIBODIES FOR BINDING PATHOLOGIC FORMS OF CALCINEURIN

(71) Applicant: University of Kentucky Research Foundation, Lexington, KY (US)

(72) Inventors: Susan D. Kraner, Lexington, KY (US); Rodney P Guttmann, Cantonment, FL (US); Christopher M. Norris, Lexington, KY (US); Jenna Leigh Gollihue, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 226 days.

(21) Appl. No.: 17/325,085

(22) Filed: May 19, 2021

(65) Prior Publication Data

US 2021/0363274 A1    Nov. 25, 2021

Related U.S. Application Data

(60) Provisional application No. 63/028,079, filed on May 21, 2020.

(51) Int. Cl.
C07K 16/40    (2006.01)
C12N 15/85    (2006.01)
A61K 47/68    (2017.01)

(52) U.S. Cl.
CPC ........... *C07K 16/40* (2013.01); *A61K 47/6871* (2017.08); *C12N 15/85* (2013.01); *C07K 2317/64* (2013.01); *C12Y 301/03016* (2013.01)

(58) Field of Classification Search
CPC ............... C07K 16/40; C07K 2317/64; C07K 2317/34; C12N 15/85; A61K 47/6871
See application file for complete search history.

(56) References Cited

PUBLICATIONS

Almagro JC, Fransson J. Humanization of antibodies. Front Biosci. Jan. 1, 2008;13:1619-33. (Year: 2008).*

Chen et al. Enhancement and destruction of antibody function by somatic mutation: unequal occurrence is controlled by V gene combinatorial associations.EMBO J. Jun. 15, 1995; 14(12): 2784-94. (Year: 1995).*

Kussie et al. A single engineered amino acid substitution changes antibody fine specificity.J Immunol. Jan. 1, 1994;152(1):146-52. (Year: 1994).*

Edwards et al. The remarkable flexibility of the human antibody repertoire;isolation of over one thousand different antibodies to a single protein,BLyS. J Mol Biol Nov. 14, 2003;334(1):103-18. (Year: 2003).*

Koenig et al. Mutational landscape of antibody variable domains reveals a switch modulating the interdomain conformational dynamics and antigen binding. PNAS Jan. 24, 2017 114(4)E486-E495;f irstpublished Jan. 5, 2017. (Year: 2017).*

Wu et al., Critical Role of Calpain-mediated Cleavage of Calcineurin in Excitotoxic Neurodegeneration, JBC 279: 4929-4940, 2004.

Melanie M. Pleiss, Pradoldej Sompol, Susan D. Kraner, Hafiz Mohmmad Abdul, Jennifer L. Furman, Rodney P. Guttmann, Donna M. Wilcock, Peter T. Nelson, Christopher M. Norris, Calcineurin proteolysis in astrocytes: Implications for impaired synaptic function, Biochimica et Biophysica Acta: 1521-1532, 2016.

Gollihue, J., Kraner, S., Weiss, B., Artuishin, I., Sompol, P., Norris, C. "Development of Monoclonal Antibodies Specific for the Calpain-Generated Δ48 kDa Calcineurin Fragment, a Marker of Distressed Astrocytes." Alzheimer's Association International Conference, Virtual, Jul. 2020.

* cited by examiner

*Primary Examiner* — Aurora M Fontainhas
*Assistant Examiner* — Jennifer A Benavides
(74) *Attorney, Agent, or Firm* — Stites & Harbison PLLC; Mandy Wilson Decker

(57) ABSTRACT

Provided herein are antibodies, or antigen-binding portions thereof, which specifically bind to pathologic forms of calcineurin. The invention further provides a method of obtaining such antibodies and nucleic acids encoding the same. The invention further relates to compositions and methods for use of these antibodies.

9 Claims, 8 Drawing Sheets
Specification includes a Sequence Listing.

ANTIBODIES FOR BINDING PATHOLOGIC FORMS OF CALCINEURIN

RELATED APPLICATIONS

This application claims priority from U.S. Provisional Application Ser. No. 63/028,079 filed May 21, 2020, the entire disclosure of which is incorporated herein by this reference.

GOVERNMENT INTEREST

This invention was made with government support under grant number RF1-AG027297 awarded by the National Institutes of Health. The government has certain rights in the invention.

TECHNICAL FIELD

The presently-disclosed subject matter relates to antibodies that are useful for binding pathologic forms of calcineurin.

INTRODUCTION

Calcineurin (CN) is a 60 kDa enzyme that shows little activity when intracellular calcium levels are low. CN activity is catalyzed by binding calcium/calmodulin during elevations in cellular calcium. High activity levels of CN in brain lead to neuroinflammation, neuronal hyperexcitability, and cognitive loss. Pathologically high levels of CN activity occur when calcineurin is proteolyzed to a 45-48 kDa fragment called delta-CN.

The epitope identified by most commercially-available CN antibodies is located in the carboxy termus region of CN. These C-terminus antibodies detect full length (normal) CN, but do not detect delta-CN. There have been a few attempts to provide an antibody that recognizes an epitope in the amino terminus of CN. These N-terminus antibodies are non-specific, in that they bind both full length CN and delta-CN.

Use of N terminus antibodies in Western blot applications has revealed high levels of delta-CN in postmortem human brain homogenates at early stages of Alzheimer's disease. Similar elevations in delta-CN are found in rodent models of Alzheimer's, stroke, traumatic brain injury, and other forms of neurodegeneration. N-terminus antibodies are useful for detecting pathological CN in Western blots, but cannot distinguish between full length CN and pathological delta-CN in immunohistochemistry and ELISA applications.

Such limitations associated with currently-available CN antibodies have made it impossible to determine where pathologic delta-CN fragments are generated. Thus, it remains unknown whether delta-CN is generated in specific cell types or in close proximity to other forms of neuropathology. Furthermore, currently-available CN antibodies cannot be used to effectively determine how delta-CN mechanistically contributes to brain pathophysiology.

Accordingly, there remains a need in the art for an antibody that does not bind full-length/normal CN, but is specific for pathologic delta-CN fragments, which can be used in conjunction with immunohistochemistry to determine where delta-CN is generated in relation to different cell types and/or to study developing neuropathology.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes monoclonal antibodies that bind pathologic delta-CN fragments, but do not bind full-length (normal) CN. In conjunction with immunohistochemistry, antibodies of the instant invention can pinpoint where delta-CN is generated in relation to different cell types and/or developing neuropathology.

The presently-disclosed subject matter provides antibodies, or antigen-binding portions thereof, which specifically bind to pathologic forms of calcineurin. The invention further provides a method of obtaining such antibodies and nucleic acids encoding the same. The invention further relates to compositions and methods for use of these antibodies.

The presently-disclosed subject matter includes isolated nucleic acid molecules. In some embodiments, the isolated nucleic acid molecule encoding a heavy chain, a light chain, or both a heavy chain and a light chain of an antibody or an antigen-binding portion thereof that specifically binds pathologic forms of calcineurin. In some embodiments, the isolated nucleic acid molecule comprises: (a) the nucleotide sequence of SEQ ID NO: 2; (b) the nucleotide sequence of SEQ ID NO: 4; (c) the nucleotide sequence pairs SEQ ID NOs: 2 and 4; (d) the nucleotide sequence of SEQ ID NO: 6; (e) the nucleotide sequence of SEQ ID NO: 8; or (f) the nucleotide sequence pairs SEQ ID NOs: 6 and 8.

The presently-disclosed subject matter includes vectors. In some embodiments, the vector comprises a nucleic acid as disclosed herein. The presently-disclosed subject matter includes host cells. In some embodiments, the host cell comprises a nucleic acid as disclosed herein or a vector as disclosed herein. In some embodiments, the host cell is a mammalian cell.

The presently-disclosed subject matter includes of producing an antibody or an antigen-binding portion thereof that specifically binds pathologic forms of calcineurin. In some embodiments, the method includes (a) culturing a host cell as disclosed herein under conditions that allow said antibody or antigen-binding portion to be expressed, wherein the host cell comprises nucleotide sequences coding the heavy chain and light chain of the antibody or antigen-binding portion, and (b) isolating said antibody or antigen-binding portion from the culture.

The presently-disclosed subject matter includes or antigen fragment thereof. In some embodiments, the antibody is selected from the group consisting of: (a) an antibody comprising the sequence of SEQ ID NO: 3; (b) an antibody comprising the sequence of SEQ ID NO: 5, (c) an antibody comprising the sequence of SEQ ID NOs: 3 and 5; (d) an antibody comprising the sequence of SEQ ID NO: 7; (e) an antibody comprising the sequence of SEQ ID NO: 9; (f) an antibody comprising the sequence of SEQ ID NOs: 7 and 9.

The presently-disclosed subject matter includes a hybridoma cell line deposited with American Type Culture Collection (ATCC) under deposit number PTA-126750 or PTA-126751. The presently-disclosed subject matter includes an antibody expressed by such a hybridoma cell line. The presently-disclosed subject matter includes a method of producing an antibody or an antigen-binding portion thereof that specifically binds pathologic forms of calcineurin, which involves: (a) culturing such a hybridoma cell line, and (b) isolating said antibody or antigen-binding portion from the culture.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

BRIEF DESCRIPTION OF THE SEQUENCE LISTING

Figure 1A:
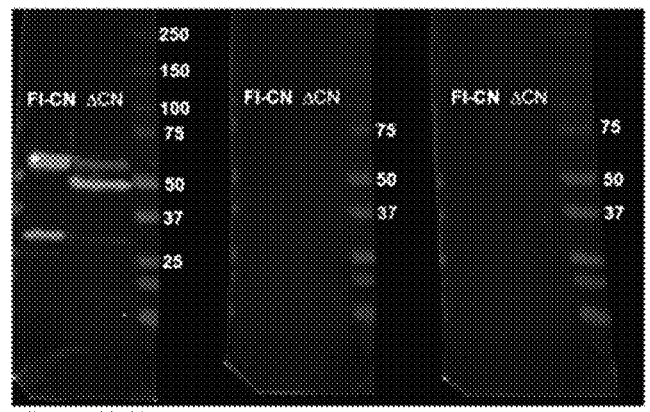
FIGS. 1A-1C include the results of a Western blot screen of mouse antisera against full-length and ΔCN.

SEQ ID NO: 1 includes the polypeptide sequence of the C-terminal end of a 48 kDa fragment of the proteolyzed calcineurin as disclosed herein.

SEQ ID NO: 2 includes the nucleic acid sequence encoding the polypeptide sequence of the heavy chain of an antibody that is referred to herein as 17E1.

SEQ ID NO: 3 includes the polypeptide sequence of the heavy chain of an antibody that is referred to herein as 17E1.

SEQ ID NO: 4 includes the nucleic acid sequence encoding the polypeptide sequence of the light chain of an antibody that is referred to herein as 17E1.

SEQ ID NO: 5 includes the polypeptide sequence of the light chain of an antibody that is referred to herein as 17E1.

SEQ ID NO: 6 includes the nucleic acid sequence encoding the polypeptide sequence of the heavy chain of an antibody that is referred to herein as 26A6.

SEQ ID NO: 7 includes the polypeptide sequence of the heavy chain of an antibody that is referred to herein as 26A6.

SEQ ID NO: 8 includes the nucleic acid sequence encoding the polypeptide sequence of the light chain of an antibody that is referred to herein as 26A6.

SEQ ID NO: 9 includes the polypeptide sequence of the light chain of an antibody that is referred to herein as 26A6.

This application contains a sequence listing submitted in accordance with 37 C.F.R. 1.821, named Kraner UKRF 2425 Sequence Listing_ST25..txt, created on May 17, 2021, having a size of 24 KB, which is incorporated herein by this reference.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Disclosed herein are unique and advantageous antibodies or antigen-binding portions thereof that specifically binds pathologic forms of calcineurin. The presently-disclosed subject matter includes antibodies, or antigen-binding portions thereof, which specifically bind to pathologic forms of calcineurin. The invention further provides a method of obtaining such antibodies and nucleic acids encoding the same. The invention further relates to compositions and methods for use of these antibodies.

The practice of the presently-disclosed subject matter will employ, unless otherwise indicated, conventional techniques of molecular biology (including recombinant techniques), microbiology, cell biology, biochemistry and immunology, which are within the skill of the art. Enzymatic reactions and purification techniques are performed according to manufacturer's specifications, as commonly accomplished in the art or as described herein. The nomenclatures used in connection with, and the laboratory procedures and techniques of, analytical chemistry, biochemistry, immunology, molecular biology, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

The presently-disclosed subject matter includes monoclonal antibodies that bind pathologic delta-CN fragments, but do not bind full-length (normal) CN. In conjunction with immunohistochemistry, antibodies of the instant invention can pinpoint where delta-CN is generated in relation to different cell types and/or developing neuropathology.

The presently-disclosed subject matter provides antibodies, or antigen-binding portions thereof, which specifically bind to pathologic forms of calcineurin. The invention further provides a method of obtaining such antibodies and nucleic acids encoding the same. The invention further relates to compositions and methods for use of these antibodies.

The presently-disclosed subject matter includes isolated nucleic acid molecules. In some embodiments, the isolated nucleic acid molecule encoding a heavy chain, a light chain, or both a heavy chain and a light chain of an antibody or an antigen-binding portion thereof that specifically binds pathologic forms of calcineurin. In some embodiments, the isolated nucleic acid molecule comprises: (a) the nucleotide sequence of SEQ ID NO: 2; (b) the nucleotide sequence of SEQ ID NO: 4; (c) the nucleotide sequence pairs SEQ ID NOs: 2 and 4; (d) the nucleotide sequence of SEQ ID NO: 6; (e) the nucleotide sequence of SEQ ID NO: 8; or (f) the nucleotide sequence pairs SEQ ID NOs: 6 and 8.

The presently-disclosed subject matter includes vectors. In some embodiments, the vector comprises a nucleic acid as disclosed herein. The presently-disclosed subject matter includes host cells. In some embodiments, the host cell comprises a nucleic acid as disclosed herein or a vector as disclosed herein. In some embodiments, the host cell is a mammalian cell.

The presently-disclosed subject matter includes of producing an antibody or an antigen-binding portion thereof that specifically binds pathologic forms of calcineurin. In some embodiments, the method includes (a) culturing a host cell as disclosed herein under conditions that allow said antibody or antigen-binding portion to be expressed, wherein the host cell comprises nucleotide sequences coding the heavy chain and light chain of the antibody or antigen-binding portion, and (b) isolating said antibody or antigen-binding portion from the culture.

The presently-disclosed subject matter includes or antigen fragment thereof. In some embodiments, the antibody is selected from the group consisting of: (a) an antibody comprising the sequence of SEQ ID NO: 3; (b) an antibody comprising the sequence of SEQ ID NO: 5, (c) an antibody comprising the sequence of SEQ ID NOs: 3 and 5; (d) an antibody comprising the sequence of SEQ ID NO: 7; (e) an antibody comprising the sequence of SEQ ID NO: 9; (f) an antibody comprising the sequence of SEQ ID NOs: 7 and 9.

The presently-disclosed subject matter includes a hybridoma cell line deposited with American Type Culture Collection (ATCC) under deposit number PTA-126750 or PTA-126751. The presently-disclosed subject matter includes an antibody expressed by such a hybridoma cell line. The presently-disclosed subject matter includes a method of producing an antibody or an antigen-binding portion thereof that specifically binds pathologic forms of calcineurin, which involves: (a) culturing such a hybridoma cell line, and (b) isolating said antibody or antigen-binding portion from the culture.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

In certain instances, nucleotides and polypeptides disclosed herein are included in publicly-available databases, such as GENBANK® and SWISSPROT. Information including sequences and other information related to such nucleotides and polypeptides included in such publicly-available databases are expressly incorporated by reference. Unless otherwise indicated or apparent the references to such publicly-available databases are references to the most recent version of the database as of the filing date of this Application.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, in some embodiments ±0.1%, in some embodiments ±0.01%, and in some embodiments ±0.001% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

An "antibody" is an immunoglobulin molecule capable of specific binding to a target, such as a carbohydrate, polynucleotide, lipid, polypeptide, etc., through at least one antigen recognition site, located in the variable domain of the immunoglobulin molecule. As used herein, the term encompasses not only intact polyclonal or monoclonal antibodies, but also, unless otherwise specified, any antigen-binding portion thereof that competes with the intact antibody for specific binding, fusion proteins comprising an antigen-binding portion, and any other modified configuration of the immunoglobulin molecule that comprises an antigen recognition site. Antigen-binding portions include, for example, Fab, Fab', F(ab')$_2$, Fd, Fv, domain antibodies (dAbs, e.g., shark and camelid antibodies), portions including complementarity determining regions (CDRs), single chain variable fragment antibodies (scFv), maxibodies, minibodies, intrabodies, diabodies, triabodies, tetrabodies, v-NAR and bis-scFv, and polypeptides that contain at least a portion of an immunoglobulin that is sufficient to confer specific antigen binding to the polypeptide. Depending on the antibody amino acid sequence of the constant region of its heavy chains, immunoglobulins can be assigned to different classes. There are five major classes (i.e., isotypes) of immunoglobulins: IgA, IgD, IgE, IgG, and IgM, and several of these may be further divided into subclasses (subtypes), e.g., IgG$_1$, IgG$_2$, IgG$_3$, IgG$_4$, IgA$_1$ and IgA$_2$. The heavy-chain constant regions that correspond to the different classes of immunoglobulins are called alpha, delta, epsilon, gamma, and mu, respectively. The subunit structures and three-dimensional configurations of different classes of immunoglobulins are well known.

The terms "antigen-binding portion" or "antigen-binding fragment" of an antibody (or simply "antibody portion"), as used interchangeably herein, refers to one or more portions of an antibody that retain the ability to specifically bind to an antigen (e.g., delta-CN). It has been shown that the antigen-binding function of an antibody can be performed by portions of a full-length antibody.

A "variable domain" of an antibody refers to the variable domain of the antibody light chain ($V_L$) or the variable domain of the antibody heavy chain ($V_H$), either alone or in combination. As known in the art, the variable domains of the heavy and light chains each consist of four framework regions (FRs) connected by three complementarity determining regions (CDRs) also known as hypervariable regions, and contribute to the formation of the antigen-binding site of antibodies. If variants of a subject variable domain are desired, particularly with substitution in amino acid residues outside a CDR (i.e., in the framework region), appropriate amino acid substitution, in some embodiments, conservative amino acid substitution, can be identified by comparing the subject variable domain to the variable domains of other antibodies which contain CDR1 and CDR2 sequences in the same canonical class as the subject variable domain.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen binding residues.

The term "antigen (Ag)" refers to the molecular entity used for immunization of an immunocompetent vertebrate to produce the antibody (Ab) that recognizes the Ag or to screen an expression library (e.g., phage, yeast or ribosome display library, among others). Herein, Ag is termed more broadly and is generally intended to include target molecules that are specifically recognized by the Ab, thus including portions or mimics of the molecule used in an immunization process for raising the Ab or in library screening for selecting the Ab.

Generally, the term "epitope" refers to the area or region of an antigen to which an antibody specifically binds, i.e., an area or region in physical contact with the antibody. Thus, the term "epitope" refers to that portion of a molecule capable of being recognized by and bound by an antibody at one or more of the antibody's antigen-binding regions.

An antibody that "preferentially binds" or "specifically binds" (used interchangeably herein) to an epitope is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. Also, an antibody "specifically binds" or "preferentially binds" to a target if it binds with greater affinity, avidity, more readily, and/or with greater duration to that target in a sample than it binds to other substances present in the sample. As such, "specific binding" or "preferential binding" does not necessarily require (although it can include) exclusive binding.

A variety of assay formats may be used to select an antibody or peptide that specifically binds a molecule of interest. For example, solid-phase ELISA immunoassay, immunoprecipitation, Biacore™ (GE Healthcare, Piscataway, N.J.), KinExA, fluorescence-activated cell sorting (FACS), Octet™ (FortéBio, Inc., Menlo Park, Calif.) and Western blot analysis are among many assays that may be used to identify an antibody that specifically reacts with an antigen or a receptor, or ligand binding portion thereof, that specifically binds with a cognate ligand or binding partner.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected and/or transformed in vivo with a polynucleotide of this disclosure.

As used herein, "vector" means a construct, which is capable of delivering, and, in some embodiments, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. In some embodiments, diluents for aerosol or parenteral administration are phosphate buffered saline (PBS) or normal (0.9%) saline. Compositions comprising such carriers are formulated by well-known conventional methods.

The presently-disclosed subject matter is further illustrated by the following specific but non-limiting examples. The following examples may include compilations of data that are representative of data gathered at various times during the course of development and experimentation related to the present invention.

EXAMPLES

Monoclonal antibodies to Δ48 kDa Calcineurin were prepared as follows. Immunization was carried out by Genscript using the peptide CGGGESVLTLK (SEQ ID NO: 1), which represents the C-terminal end of a 48 kDa fragment of proteolyzed calcineurin. This peptide was conjugated to KLH and injected into three (3) Balb/c mice and three (3) C57 Mice.

ELISA Screens were carried out by Genscript to the peptide CGGGESVLTLK (SEQ ID NO: 1). Western screens to endogenous proteolyzed Δ48 kDa calcineurin were carried out using extracts from 2 year old 5X FAD mice brains, which have exceptionally high amounts of this fragment.

Figure 1B:
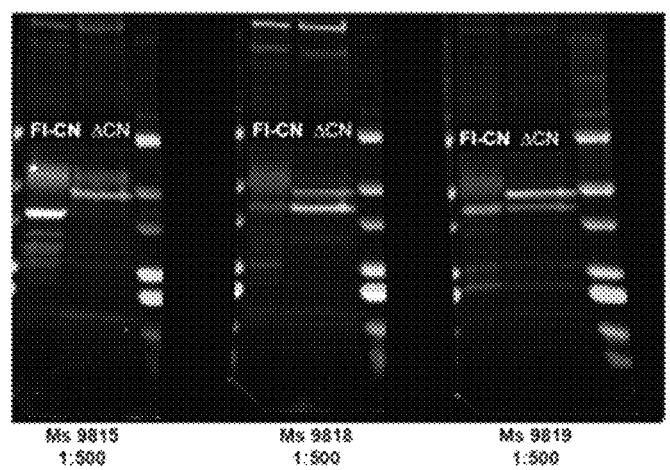
Figure 1C:
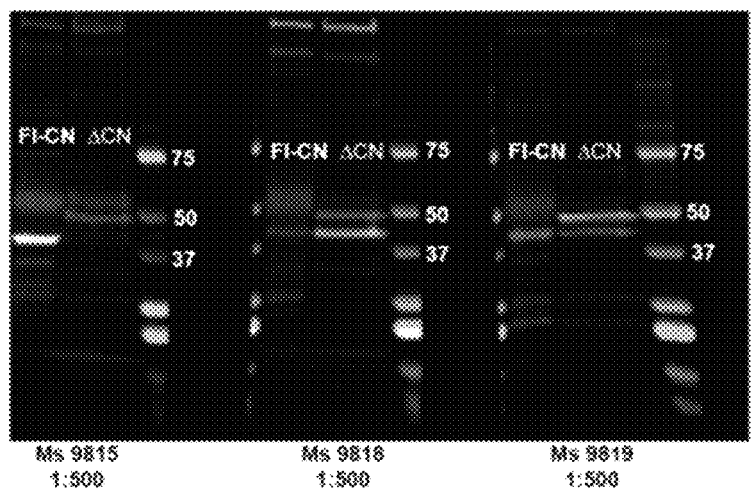

Initial ELISA screens of the mouse antisera gave low results, which is likely due to the inability of the mice to make an antibody to a sequence so similar to their endogenous sequence. However, a Western screen was conducted and turned out well. Two immunoreactivities of interest were identified, one at 48 kDa and one at 45 kDa. Because of these Western results, it was possible to get a Δ48 kDa-specific calcineurin antibody. The Western data are provided in FIGS. 1A-1C, and the ELISA data are provided in Table 1.

TABLE 1

Results of Initial ELISA Screen of Mice

| Animal Number | Signal in 1:1000 dilution |
|---|---|
| #9815 | 0.333 |
| #9816 | 0.086 |
| #9817 | 0.058 |
| #9818 | 1.499 |
| #9819 | 0.612 |
| #9820 | 0.108 |

Figure 2:
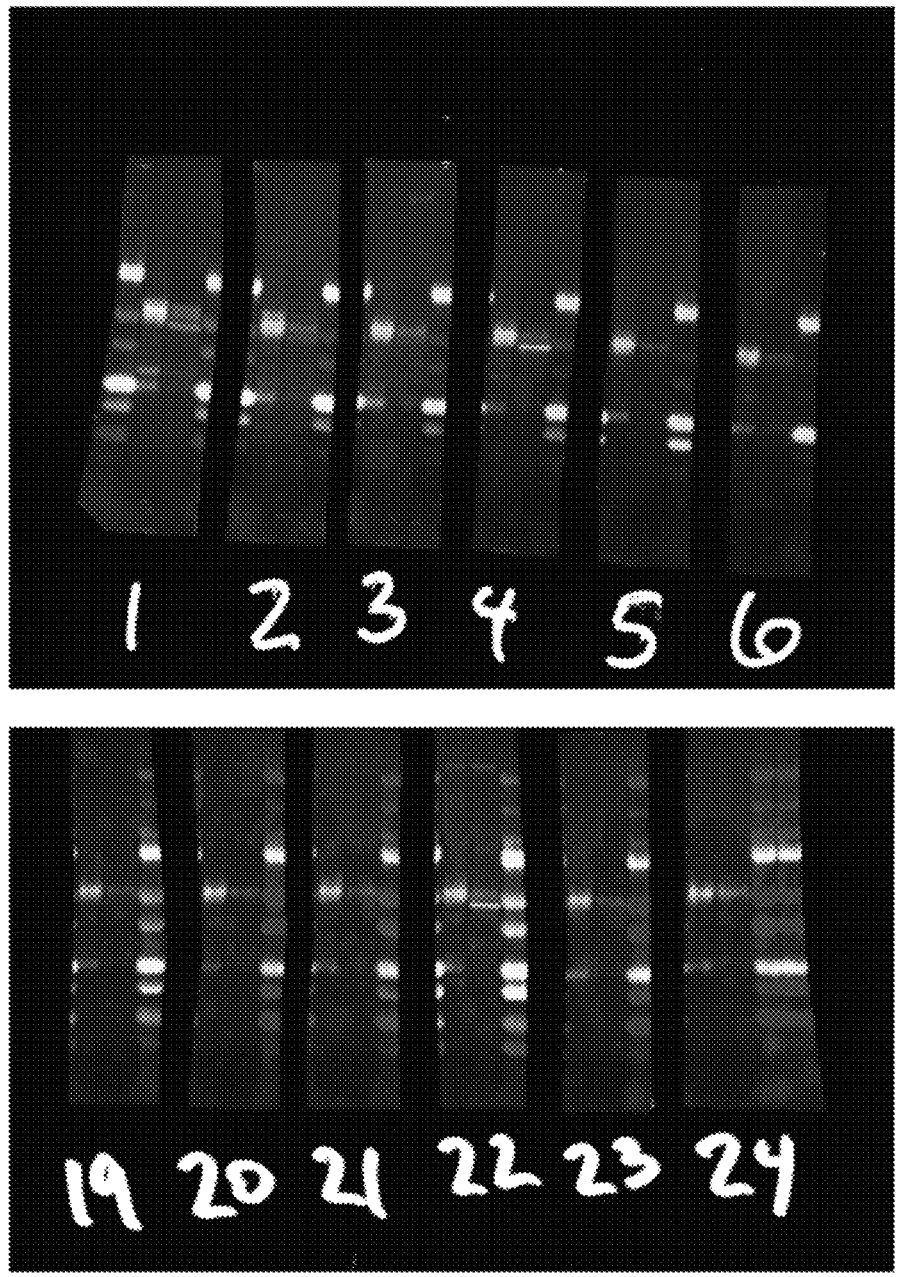
FIG. 2 includes the results of initial screens of hybridoma supernatants. Each Western blot includes: lane 1, full length CN, lane 2, Δ48 kDa CN, and lane 3 MWS.

Animals 9818 and 9819 were selected to take forward into hybridoma fusion. Hybridoma supernatants were screened in "mini" western blots. Each western blot included: lane 1, full length CN; lane 2, Δ48 kDa CN; and lane 3 MWS. A total of 48 supernatants were screened, and the two (2) positives selected are shown in FIG. 2. The antibody shown in lane 4 is 17E1 and the antibody shown in lane 22 is 26A6. Western screening was repeated. The final positive subclone screen and selection of the final antibodies was conducted.

Figure 3:
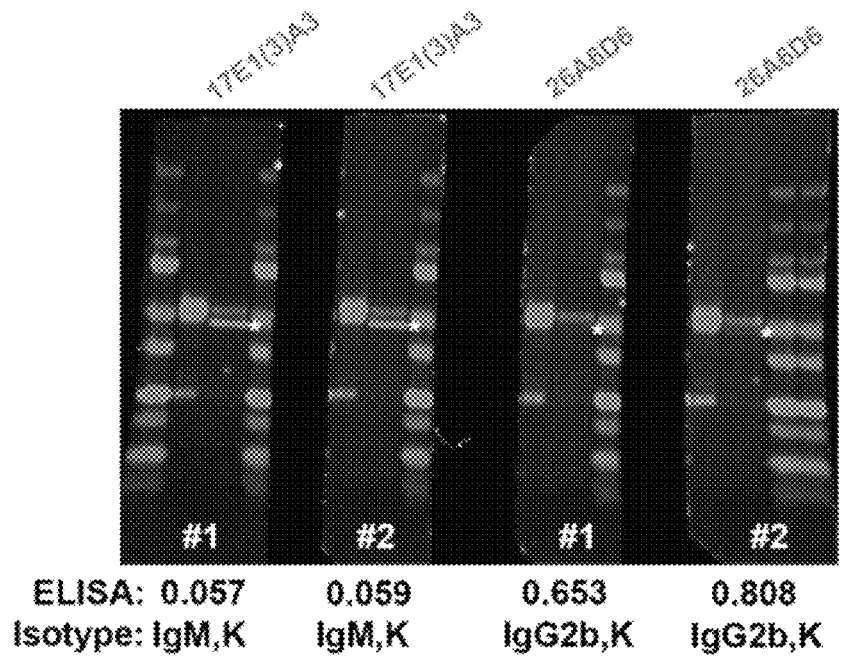
FIG. 3 includes the results of a Western blot of mAB final subclones.
Figure 4:
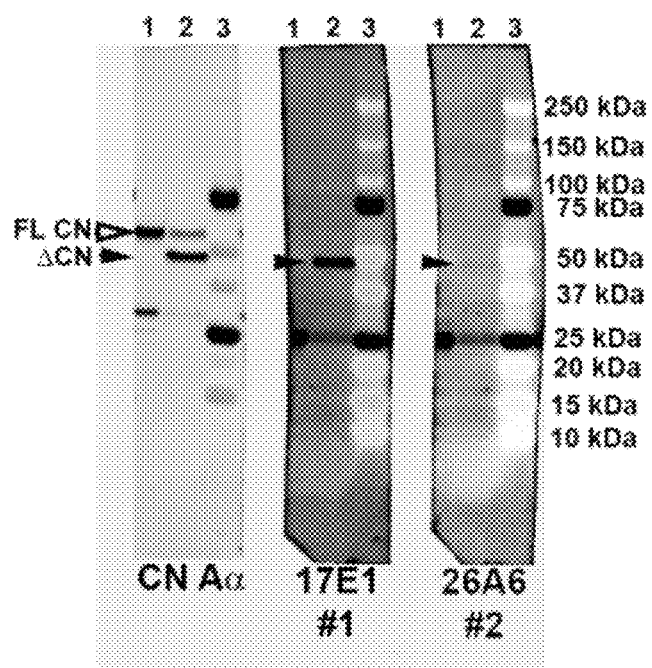
FIG. 4 includes the results of a Western blot of new ΔCN Monoclonal antibodies. Lane 1: Membrane-cytosol fraction 5xFAD Mice, which has full length CN. Lane 2: Nuclear Fraction 5xFAD Mice, which has Δ48 kDa CN. Lane 3: Molecular Weight Standards.

FIG. 3 shows IgG heavy chains in western blots. A problem with these blots is that the IgG heavy chain that runs at 50 kDa undermines the appearance of the blots in terms of showing the appearance of the 60 kDa versus 48 kDa bands. Therefore, future blots were conducted with a light chain-specific second antibody. With reference to FIG. 4, subsequent blots more clearly show that the monoclonal antibodies do not see anything but the 48 kDa band (the 25 kDa band is the antibody light chain). As shown in FIG. 4, it is clear that the clones do not react with the 60 kDa full length calcineurin. Monoclonal antibody 17E1 is very strong in the Western, while 26A6 is stronger in the ELISA.

Figure 5A:
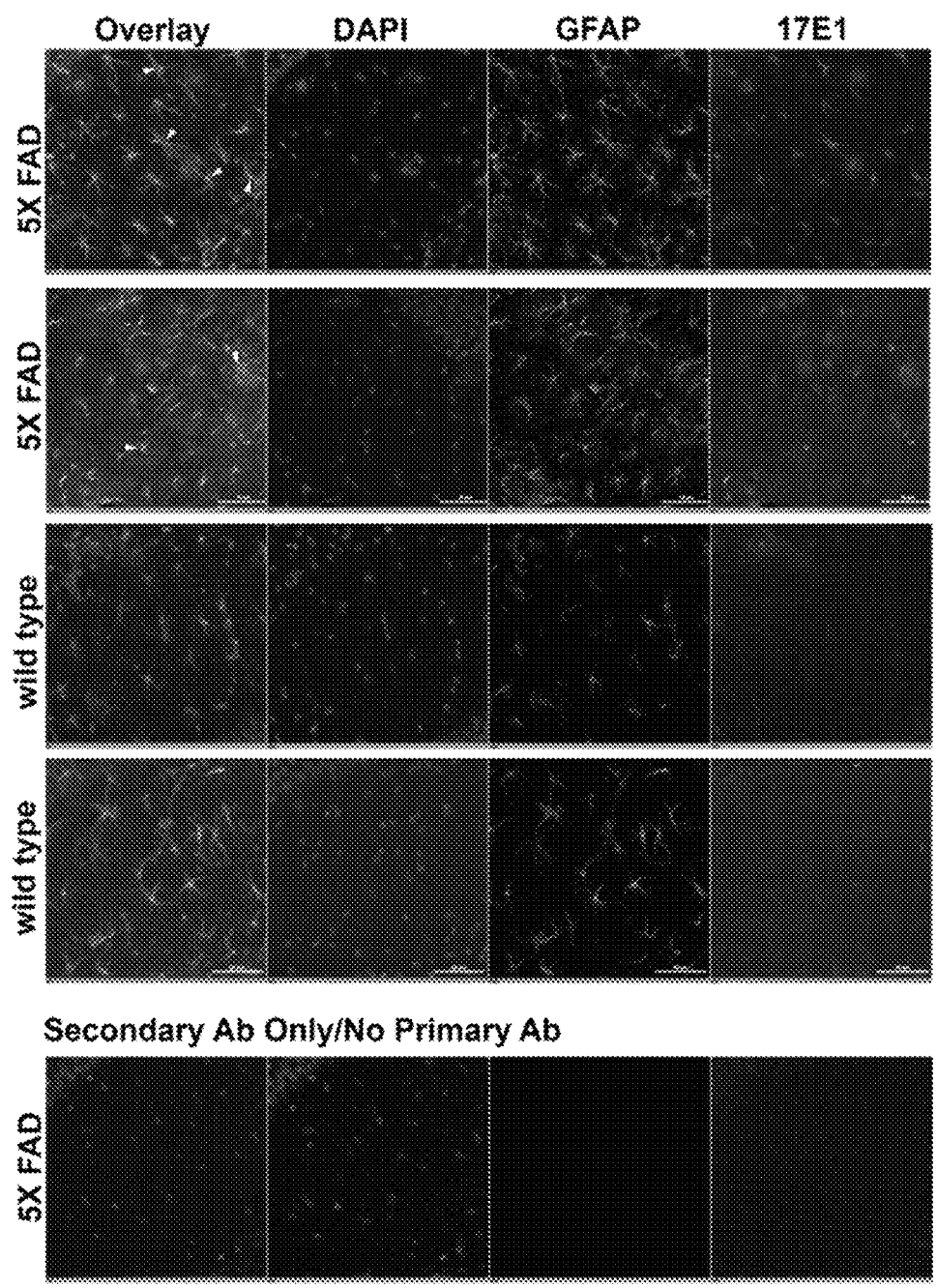
FIG. 5A includes results showing that the monoclonal antibody 17E1 detects astrocytes in 5X FAD but not wild type mice.

With reference to FIG. 5A, monoclonal antibody 17E1 detects astrocytes in 5X FAD but not wild type mice. 12-14 month old 5X FAD and wild type littermate controls were perfused with ice cold saline and brains harvested into 4% paraformaldehyde. After 24 hrs, the brains were transferred to 30% sucrose until saturated, sectioned in 40 μm sections, and stored in antifreeze at −20 C until used for labeling. Following optimization of staining including antigen retrieval, the following were shown: DAPI in blue, rabbit anti-GFAP (Cell Signaling) in green, and protein L-purified 17E1 mAb (~10 ug/ml) in red (although FIG. 5A is present in greyscale). The GFAP antibody was counterstained with 488-conjugated goat anti-rabbit and the 17E1 with 594-conjugated goat anti-mouse.

The 17E1 mAb consistently stained 5X brain tissue, but not wild type littermate control brain tissue. 5X FAD brain tissue treated with and secondary antibodies only shows no staining. The 17E1 antibody does not stain all astrocytes uniformly. The white arrows in the overlay indicate astrocytes with yellow centers indicating especially strong co-staining with GFAP and 17E1 antibodies. There are also astrocytes that have relatively low levels of 17E1 expression. Spatial gene profiling techniques can be used to determine how the transcriptional signature in 17E1-stained cells differ from those that do not express it. It is possible that 17E1 marks astrocytes that are distressed.

Figure 5B:
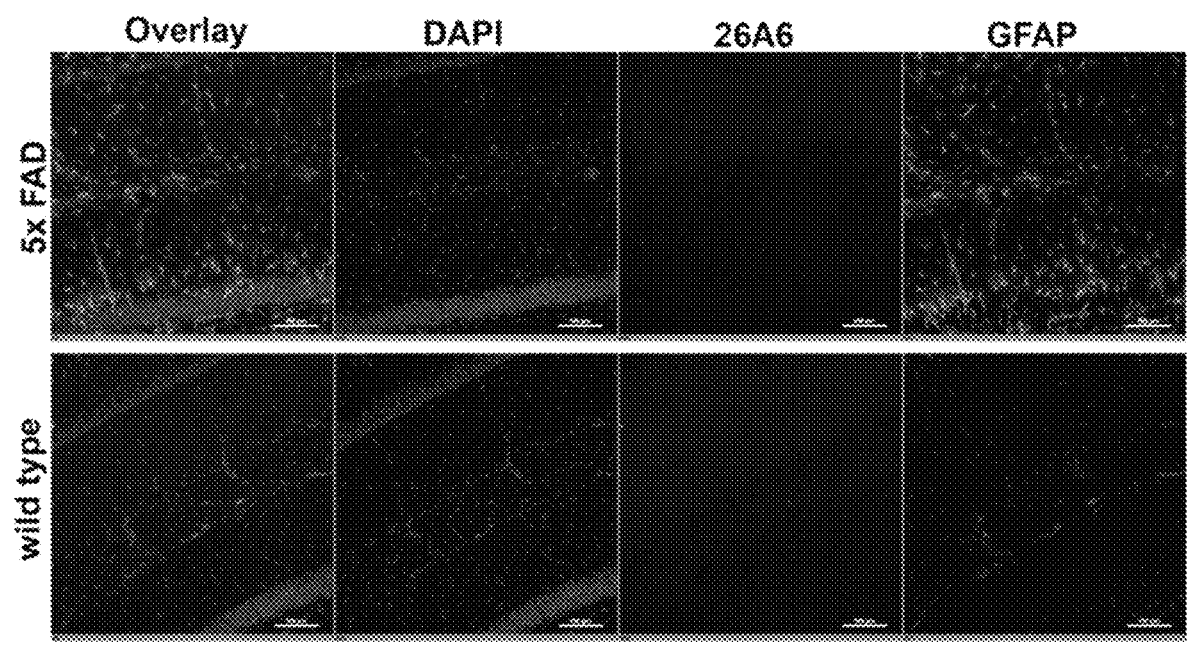
FIG. 5B includes results showing that the monoclonal antibody 26A6 does not stain 5X FAD or wild type brain tissue.

With reference to FIG. 5B, monoclonal antibody 26A6 does not stain 5X FAD or wild type brain tissue. The same tissue used for the staining carried out in panel A was stained with affinity-purified mAb 26A6. In this case, the 26A6 staining was done in the green channel since the analysis was carried out with a tyramide signal amplification kit (Invitrogen Superboost Kit, 488-conjuated goat anti-mouse). The GFAP was counterstained with 594-conjugated anti-rabbit in the red channel. No signal was detected, even with this signal amplification approach (and multiple tries with various antigen-retrieval approaches). Although signal was not detected with the 26A6 antibody under these conditions and in this type of tissue, it could be used in other types of neurodegenerative conditions.

Figure 6:
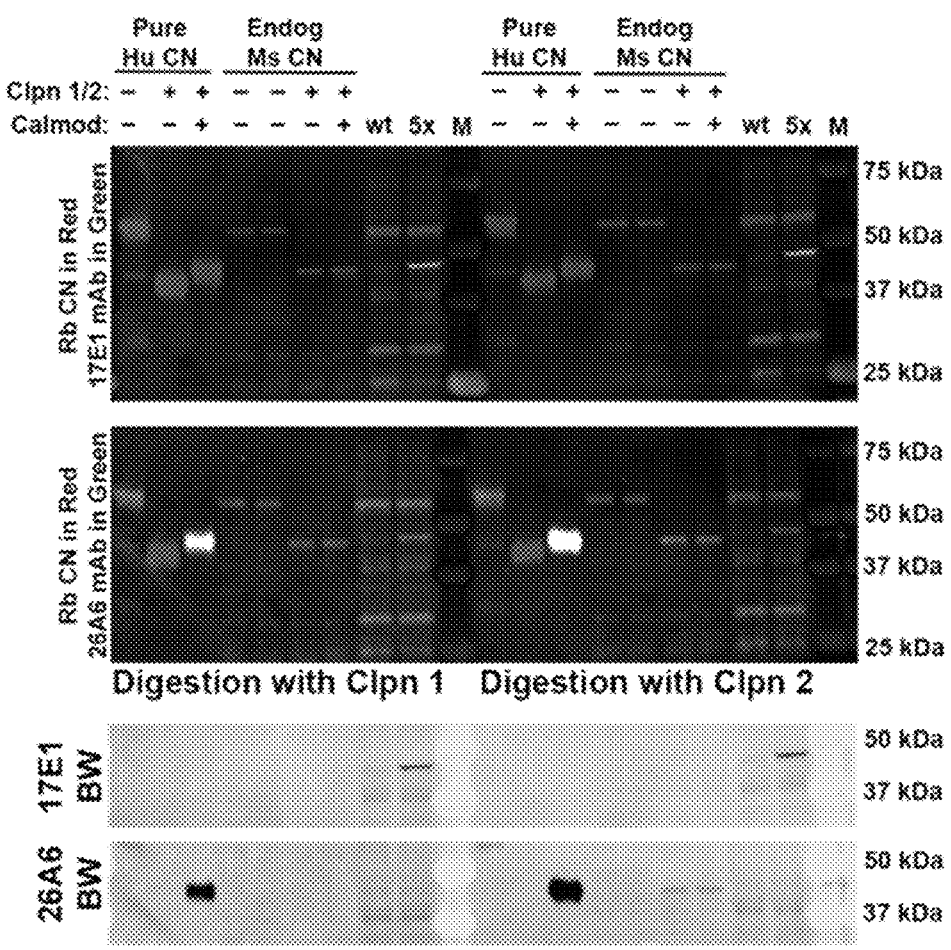
FIG. 6 includes results showing that 26A6 reacts to classic calpain-cleaved calcineurin site, while 17E1 detects a cleavage site unique to 5X tissue.

With reference to FIG. 6, it was determined that 26A6 reacts to classic calpain-cleaved calcineurin site, while 17E1 detects a cleavage site unique to 5X tissue. The peptide which was used as an antigen was based on the cleavage site of the 48 kDa calpain-cleavage product of calcineurin reported by Wu et al., Critical Role of Calpain-mediated Cleavage of Calcineurin in Excitotoxic Neurodegeneration, JBC 279: 4929-4940, 2004. This site was also cleaved in vitro by calpain, in the presence of calmodulin (Wu et al., 2004). To confirm that these mAbs reacted with the cleavage site to which they were targeted, both recombinant human calcineurin (CN) and endogenous mouse brain calcineurin were taken, and cleavage was performed with purified calpain 1 or calpain 2 (Clpn 1 or 2). For pure human calcineurin, the inclusion of purified calmodulin altered the cleavage site, as reported previously (Wu et al., 2004), while the endogenous mouse brain calcineurin was 48 kDa in both the presence and absence of added calmodulin. This result may indicate that endogenous calmodulin was associated with the endogenous mouse calcineurin. 26A6 only detected the 48 kDa form of calcineurin, consistent with the cleavage site reported previously (ending at $K_{424}$) and consistent with its observed reactivity to the peptide $ESVLTLK_{424}$ with which the animal was immunized. Surprisingly, mAb 17E1 did not react with the calcineurin cleaved in vitro with calpain 1 or calpain 2, but did bind the 48 kDa band present in 5X FAD (5x) tissue. Looking closely at the gel, it is apparent that the band identified by 17E1 is slightly larger than that bound by 26A6. It is contemplated that the 17E1-detected fragment is post-translationally altered, e.g., the C-terminus may be acetylated on the lysine or phosphorylated on either the serine or threonine.

Figure 7A:
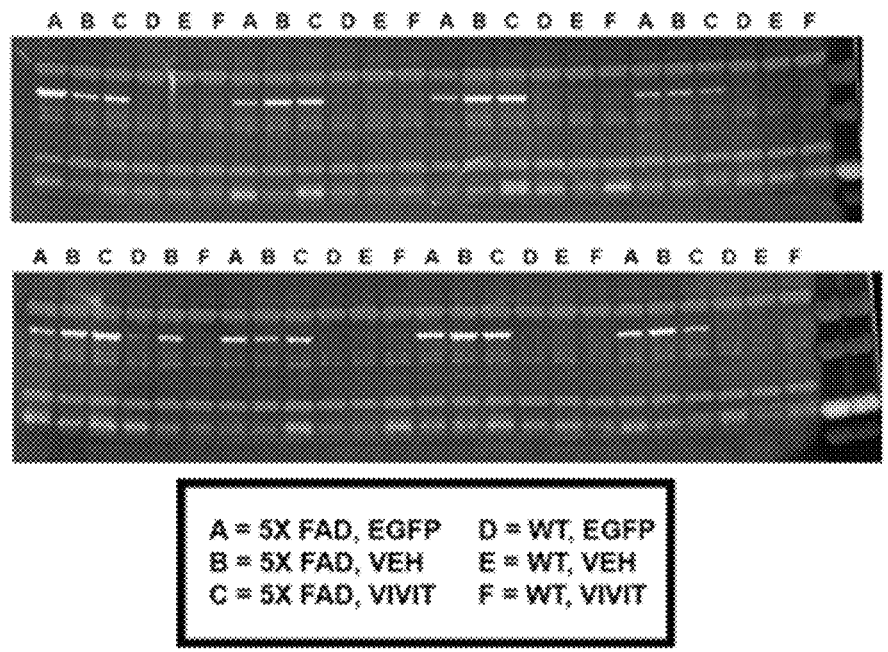
FIGS. 7A and 7B include results confirming that 17E1 mAb and Rb N-terminal Ab are both detecting 48 kDa calcineurin.
Figure 7B:
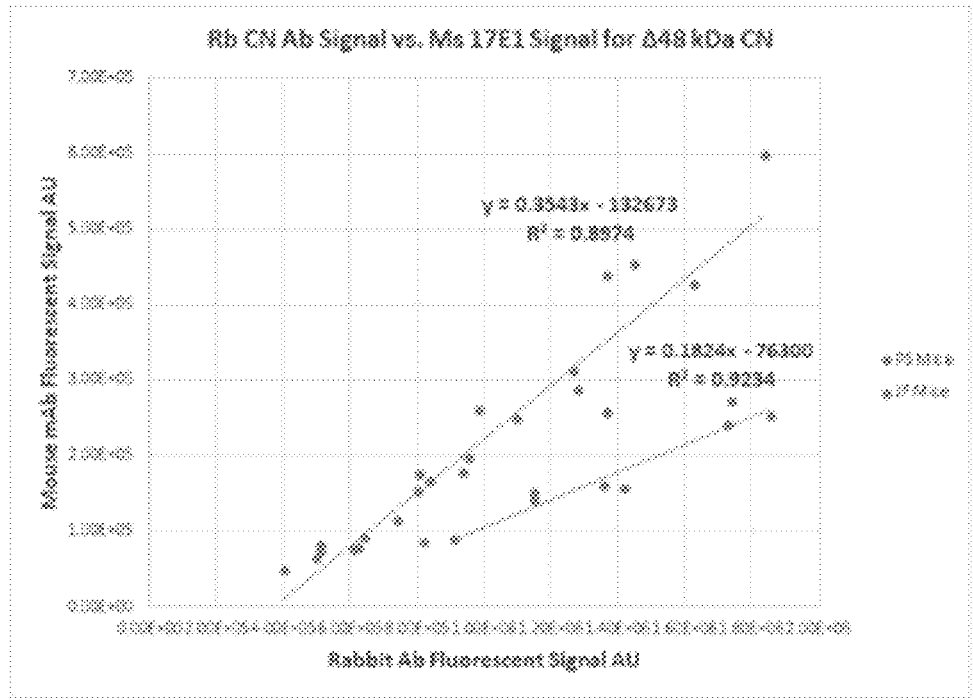

With reference to FIG. 7, co-linear detection of 17E1 mAb Target and Rb N-terminal Ab was conducted. To provide support that the 48 kDa band detected by the 17E1 mAb and the Rb calcineurin N-terminal antibody are the same protein, panels of 5X FAD versus wild type tissue were probed with both antibodies. Two sets of mice were used for this experiment. There was co-linear expression of the fragments, as shown by the high $R^2$ values, indicating that these antibodies appear to be detecting the same protein fragment.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

Wu et al., Critical Role of Calpain-mediated Cleavage of Calcineurin in Excitotoxic Neurodegeneration, JBC 279: 4929-4940, 2004

DEPOSIT INFORMATION

Hybridoma cell lines for 17E1 and 26A6 were deposited with the American Type Culture Collection (ATCC), 10801 University Boulevard, Manassas, VA 20110, USA, on Apr. 3, 2020, and given Patent Deposit Nos. PTA-126750 and PTA-126751, respectively. Applicant has or intends to comply with all the requirements set forth in 37 C.F.R. §§1.801-1.809.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. An isolated nucleic acid encoding a heavy chain, a light chain, or both a heavy chain and a light chain of an antibody or an antigen-binding portion thereof that specifically binds pathologic forms of calcineurin, wherein said nucleic acid comprises: (a) the nucleotide sequence pairs SEQ ID NOs: 2 and 4; (b) the nucleotide sequence pairs SEQ ID NOs: 6 and 8.

2. A vector comprising the nucleic acid of claim 1.

3. A host cell comprising the nucleic acid of claim 2.

4. The host cell of claim 3, wherein the cell is a mammalian cell.

5. A method of producing an antibody or an antigen-binding portion thereof that specifically binds pathologic forms of calcineurin, said method comprising: (a) culturing the host cell of claim 4 under conditions that allow said antibody or antigen-binding portion to be expressed, wherein the host cell comprises nucleotide sequences coding the heavy chain and light chain of the antibody or antigen-binding portion, and (b) isolating said antibody or antigen-binding portion from the culture.

6. An isolated antibody or antigen fragment thereof, wherein the antibody is selected from the group consisting of: (a) an antibody comprising the sequence of SEQ ID NOs: 3 and 5; or (b) an antibody comprising the sequence of SEQ ID NOs: 7 and 9.

7. A hybridoma cell line deposited with American Type Culture Collection (ATCC) under deposit number PTA-126750 or PTA-126751.

8. An antibody expressed by the hybridoma cell line of claim 7.

9. A method of producing an antibody or an antigen-binding portion thereof that specifically binds pathologic forms of calcineurin, said method comprising:
(a) culturing the hybridoma cell line of claim 7, and (b) isolating said antibody or antigen-binding portion from the culture.

* * * * *

SEQUENCE LISTING

```
<160> NUMBER OF SEQ ID NOS: 9

<210> SEQ ID NO 1
<211> LENGTH: 11
<212> TYPE: PRT
<213> ORGANISM: Artificial Sequence
<220> FEATURE:
<223> OTHER INFORMATION: Synthesized

<400> SEQUENCE: 1

Cys Gly Gly Gly Glu Ser Val Leu Thr Leu Lys
1               5                   10

<210> SEQ ID NO 2
<211> LENGTH: 1779
<212> TYPE: DNA
<213> ORGANISM: Artificial Sequence
<220> FEATURE:
<223> OTHER INFORMATION: 17E1 Heavy chain

<400> SEQUENCE: 2
atgggatgga gctggatctt tctctttctc ctgtcaggaa ctgcaggtgt cctctctgag     60
gtccagctgc aacaatctgg acttgagctg gtgaagcctg ggggttcagt gaagatatcc    120
tgtaaggctt ctggatacac gttcactgac tattacatga actgggtgaa gcagagccat    180
ggaaagagcc ttgagtggag tggagaaatt aatcctaaca atggtgatac taaatacaac    240
cagaaattta agggcaaggc cacattgact gtagacaagt cctccagtac agcctacatg    300
gagctccgca gcctgacatc tgaggactct gcagtctatt actgtgcaag aggggactat    360
ggtaaaggat ttgcttactg gggccaaggg actctggtca ctgtctctgc agagagtcag    420
tccttcccaa atgtcttccc cctcgtctcc tgcgagagcc cctgtctga taagaatctg    480 gtggccatgg gctgcctggc ccgggacttc ctgcccagca ccatttcctt cacctggaac    540
```

-continued

```
taccagaaca acactgaagt catccagggt atcagaacct tcccaacact gaggacaggg    600
ggcaagtacc tagccacctc gcaggtgttg ctgtctccca agagcatcct tgaaggttca    660
gatgaatacc tggtatgcaa atccactac ggaggcaaaa acaaagatct gcatgtgccc    720
attccagctg tcgcagagat gaaccccaat gtaaatgtgt tcgtcccacc acgggatggc    780
ttctctggcc ctgcaccacg caagtctaaa ctcatctgcg aggccacgaa cttcactcca    840
aaaccgatca cagtatcctg gctaaaggat gggaagctcg tggaatctgg cttcaccaca    900
gatccggtga ccatcgagaa caaaggatcc acaccccaaa cctacaaggt cataagcaca    960
cttaccatct ctgaaatcga ctggctgaac ctgaatgtgt acacctgccg tgtggatcac    1020
aggggtctca ccttcttgaa gaacgtgtcc tccacatgtg ctgccagtcc ctccacagac    1080
atcctaacct tcaccatccc cccctccttt gccgacatct tcctcagcaa gtccgctaac    1140
ctgacctgtc tggtctcaaa cctggcaacc tatgaaaccc tgaatatctc ctgggcttct    1200
caaagtggtg aaccactgga aaccaaaatt aaaatcatgg aaagccatcc caatggcacc    1260
ttcagtgcta agggtgtggc tagtgtttgt gtggaagact ggaataacag aaggaatttt    1320
gtgtgtactg tgactcacag ggatctgcct tcaccacaga gaaaattcat ctcaaaaccc    1380
aatgaggtgc acaaacatcc acctgctgtg tacctgctgc caccagctcg tgagcaactg    1440
aacctgaggg agtcagccac agtcacctgc ctggtgaagg gcttctctcc tgcagacatc    1500
agtgtgcagt ggcttcagag agggcaactc ttgccccaag agaagtatgt gaccagtgcc    1560
ccgatgccag agcctggggc ccaggcttc tactttaccc cacagcatcct gactgtgaca    1620
gaggaggaat ggaactccgg agagacctat acctgtgttg taggccacga ggccctgcca    1680
cacctggtga ccgagaggac cgtggacaag tccactggta acccacact gtacaatgtc    1740
tccctgatca tgtctgacac aggcggcacc tgctattga                          1779
```

<210> SEQ ID NO 3
<211> LENGTH: 592
<212> TYPE: PRT
<213> ORGANISM: Artificial Sequence
<220> FEATURE:
<223> OTHER INFORMATION: 17E1 Heavy chain

<400> SEQUENCE: 3

```
Met Gly Trp Ser Trp Ile Phe Leu Phe Leu Leu Ser Gly Thr Ala Gly
1               5                   10                  15

Val Leu Ser Glu Val Gln Leu Gln Gln Ser Gly Leu Glu Leu Val Lys
            20                  25                  30

Pro Gly Gly Ser Val Lys Ile Ser Cys Lys Ala Ser Gly Tyr Thr Phe
        35                  40                  45

Thr Asp Tyr Tyr Met Asn Trp Val Lys Gln Ser His Gly Lys Ser Leu
    50                  55                  60

Glu Trp Ser Gly Glu Ile Asn Pro Asn Asn Gly Asp Thr Lys Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Ser Ala Val
            100                 105                 110

Tyr Tyr Cys Ala Arg Gly Asp Tyr Gly Lys Gly Phe Ala Tyr Trp Gly
        115                 120                 125

Gln Gly Thr Leu Val Thr Val Ser Ala Glu Ser Gln Ser Phe Pro Asn
    130                 135                 140
```

-continued

```
Val Phe Pro Leu Val Ser Cys Glu Ser Pro Leu Ser Asp Lys Asn Leu
145                 150                 155                 160

Val Ala Met Gly Cys Leu Ala Arg Asp Phe Leu Pro Ser Thr Ile Ser
            165                 170                 175

Phe Thr Trp Asn Tyr Gln Asn Asn Thr Glu Val Ile Gln Gly Ile Arg
        180                 185                 190

Thr Phe Pro Thr Leu Arg Thr Gly Lys Tyr Leu Ala Thr Ser Gln
    195                 200                 205

Val Leu Leu Ser Pro Lys Ser Ile Leu Glu Gly Ser Asp Glu Tyr Leu
210                 215                 220

Val Cys Lys Ile His Tyr Gly Lys Asn Lys Asp Leu His Val Pro
225             230                 235                 240

Ile Pro Ala Val Ala Glu Met Asn Pro Asn Val Asn Val Phe Val Pro
                245                 250                 255

Pro Arg Asp Gly Phe Ser Gly Pro Ala Pro Arg Lys Ser Lys Leu Ile
            260                 265                 270

Cys Glu Ala Thr Asn Phe Thr Pro Lys Pro Ile Thr Val Ser Trp Leu
        275                 280                 285

Lys Asp Gly Lys Leu Val Glu Ser Gly Phe Thr Thr Asp Pro Val Thr
    290                 295                 300

Ile Glu Asn Lys Gly Ser Thr Pro Gln Thr Tyr Lys Val Ile Ser Thr
305                 310                 315                 320

Leu Thr Ile Ser Glu Ile Asp Trp Leu Asn Leu Asn Val Tyr Thr Cys
            325                 330                 335

Arg Val Asp His Arg Gly Leu Thr Phe Leu Lys Asn Val Ser Ser Thr
        340                 345                 350

Cys Ala Ala Ser Pro Ser Thr Asp Ile Leu Thr Phe Thr Ile Pro Pro
    355                 360                 365

Ser Phe Ala Asp Ile Phe Leu Ser Lys Ser Ala Asn Leu Thr Cys Leu
    370                 375                 380

Val Ser Asn Leu Ala Thr Tyr Glu Thr Leu Asn Ile Ser Trp Ala Ser
385                 390                 395                 400

Gln Ser Gly Glu Pro Leu Glu Thr Lys Ile Lys Ile Met Glu Ser His
            405                 410                 415

Pro Asn Gly Thr Phe Ser Ala Lys Gly Val Ala Ser Val Cys Val Glu
        420                 425                 430

Asp Trp Asn Asn Arg Lys Glu Phe Val Cys Thr Val Thr His Arg Asp
    435                 440                 445

Leu Pro Ser Pro Gln Lys Lys Phe Ile Ser Lys Pro Asn Glu Val His
    450                 455                 460

Lys His Pro Pro Ala Val Tyr Leu Leu Pro Pro Ala Arg Glu Gln Leu
465                 470                 475                 480

Asn Leu Arg Glu Ser Ala Thr Val Thr Cys Leu Val Lys Gly Phe Ser
            485                 490                 495

Pro Ala Asp Ile Ser Val Gln Trp Leu Gln Arg Gly Gln Leu Leu Pro
        500                 505                 510

Gln Glu Lys Tyr Val Thr Ser Ala Pro Met Pro Glu Pro Gly Ala Pro
    515                 520                 525

Gly Phe Tyr Phe Thr His Ser Ile Leu Thr Val Thr Glu Glu Glu Trp
    530                 535                 540

Asn Ser Gly Glu Thr Tyr Thr Cys Val Val Gly His Glu Ala Leu Pro
545                 550                 555                 560
```

```
His Leu Val Thr Glu Arg Thr Val Asp Lys Ser Thr Gly Lys Pro Thr
            565                 570                 575

Leu Tyr Asn Val Ser Leu Ile Met Ser Asp Thr Gly Gly Thr Cys Tyr
        580                 585                 590
```

<210> SEQ ID NO 4
<211> LENGTH: 717
<212> TYPE: DNA
<213> ORGANISM: Artificial Sequence
<220> FEATURE:
<223> OTHER INFORMATION: 17E1 Light chain

<400> SEQUENCE: 4

```
atggagaaag acacactcct gctatgggtc ctgcttctct gggttccaga ttccacaggt      60
gacattgtac tgacccaatc tccagcttct ttggctgtgt ctctagggca gagggccacc     120
atctcctgca gagccagcga aagtgttgat aattttggct tagtttttat gaactggttc     180
caacagaaac caggacagcc acccaaactc ctcatctatg ctgcatccaa gctaggatcc     240
ggggtccctg ccaggtttag tggcagtggg tctgggacag acttcagcct caacatccat     300
cctatggagg aggatgatac tgcaatgtat ttctgtcagc aaaataagga ggttccgtgg     360
acgttcggtg gaggcaccaa gctggaaatc aaacgggctg atgctgcacc aactgtatcc     420
atcttcccac catccagtga gcagttaaca tctggaggtg cctcagtcgt gtgcttcttg     480
aacaacttct accccaaaga catcaatgtc aagtggaaga ttgatggcag tgaacgacaa     540
aatggcgtcc tgaacagttg gactgatcag gacagcaaag acagcaccta cagcatgagc     600
agcaccctca cgttgaccaa ggacgagtat gaacgacata acagctatac ctgtgaggcc     660
actcacaaga catcaacttc acccattgtc aagagcttca caggaatga gtgttag       717
```

<210> SEQ ID NO 5
<211> LENGTH: 238
<212> TYPE: PRT
<213> ORGANISM: Artificial Sequence
<220> FEATURE:
<223> OTHER INFORMATION: 17E1 - Light chain

<400> SEQUENCE: 5

```
Met Glu Lys Asp Thr Leu Leu Leu Trp Val Leu Leu Leu Trp Val Pro
1               5                   10                  15

Asp Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Glu Ser
        35                  40                  45

Val Asp Asn Phe Gly Phe Ser Phe Met Asn Trp Phe Gln Gln Lys Pro
    50                  55                  60

Gly Gln Pro Pro Lys Leu Leu Ile Tyr Ala Ala Ser Lys Leu Gly Ser
65                  70                  75                  80

Gly Val Pro Ala Arg Phe Ser Gly Ser Gly Ser Gly Thr Asp Phe Ser
                85                  90                  95

Leu Asn Ile His Pro Met Glu Glu Asp Asp Thr Ala Met Tyr Phe Cys
            100                 105                 110

Gln Gln Asn Lys Glu Val Pro Trp Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160
```

```
Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235

<210> SEQ ID NO 6
<211> LENGTH: 1422
<212> TYPE: DNA
<213> ORGANISM: Artificial Sequence
<220> FEATURE:
<223> OTHER INFORMATION: 26A6 - Heavy chain

<400> SEQUENCE: 6
atgggatgga gctggatctt tctcttcctc ctgtcaggaa ctgcaggtgt ccactctgag     60
gtccagctgc aacagtctgg acctgtgctg gtgaagcctg ggcttcagt gaagatgtcc    120
tgtaaggctt ctggatacac attcactgac ttctatttga actgggtgaa gcagagccat    180
ggaaagaccc ttgagtggat tggagttatt aatccttaca cggtattac tagatataac    240
cagaagttcg ggggcacggc cacattgact gttgacaagt cctccagcac agcctacatg    300
gaactcaaca gcctgacatc tgaggactct gcagtctatt actgttcaag ggggggtaag    360
acctactact ttgactactg gggccaaggc accactctca cagtctcccc agccaaaaca    420
acacccccat cagtctatcc actggcccct gggtgtggag atacaactgg ttcctctgtg    480
actctgggat gcctggtcaa gggctacttc cctgagtcag tgactgtgac ttggaactct    540
ggatccctgt ccagcagtgt gcacaccttc ccagctctcc tgcagtctgg actctacact    600
atgagcagct cagtgactgt cccctccagc acctggccaa gtcagaccgt cacctgcagc    660
gttgctcacc cagccagcag caccacggtg gacaaaaaac ttgagcccag cgggcccatt    720
tcaacaatca cccctgtcc tccatgcaag gagtgtcaca aatgcccagc tcctaacctc    780
gagggtggac catccgtctt catcttccct ccaaatatca aggatgtact catgatctcc    840
ctgacaccca aggtcacgtg tgtggtggtg gatgtgagcg aggatgaccc agacgtccgg    900
atcagctggt ttgtgaacaa cgtggaagta cacacagctc agacacaaac ccatagagag    960
gattacaaca gtactatccg ggtggtcagt gccctcccca tccagcacca ggactggatg   1020
agtggcaagg agttcaaatg caaggtcaac aacaaagacc tcccatcacc catcgagaga   1080
accatctcaa aaattaaagg gctagtcaga gctccacaag tatacatctt gccgccacca   1140
gcagagcagt gtccaggaa agatgtcagt ctcacttgcc tggtcgtggg cttcaaccct   1200
ggagacatca gtgtggagtg gaccagcaat gggcatacag aggagaacta caaggacacc   1260
gcaccagtcc tggactctga cggttcttac ttcatataca gcaagctcga tataaaaaca   1320
agcaagtggg agaaaacaga ttccttctca tgcaacgtga gacacgaggg tctgaaaaat   1380
tactacctga agaagaccat ctcccggtct ccgggtaaat ga                       1422

<210> SEQ ID NO 7
<211> LENGTH: 473
<212> TYPE: PRT
<213> ORGANISM: Artificial Sequence
```

<220> FEATURE:
<223> OTHER INFORMATION: 26A6 - Heavy chain

<400> SEQUENCE: 7

| Met | Gly | Trp | Ser | Trp | Ile | Phe | Leu | Phe | Leu | Ser | Gly | Thr | Ala | Gly |
|-----|-----|-----|-----|-----|-----|-----|-----|-----|-----|-----|-----|-----|-----|-----|
| 1   |     |     |     | 5   |     |     |     |     | 10  |     |     |     |     | 15  |

Val His Ser Glu Val Gln Leu Gln Gln Ser Gly Pro Val Leu Val Lys
                20                  25                  30

Pro Gly Ala Ser Val Lys Met Ser Cys Lys Ala Ser Gly Tyr Thr Phe
            35                  40                  45

Thr Asp Phe Tyr Leu Asn Trp Val Lys Gln Ser His Gly Lys Thr Leu
        50                  55                  60

Glu Trp Ile Gly Val Ile Asn Pro Tyr Asn Gly Ile Thr Arg Tyr Asn
65                  70                  75                  80

Gln Lys Phe Gly Gly Thr Ala Thr Leu Thr Val Asp Lys Ser Ser Ser
                85                  90                  95

Thr Ala Tyr Met Glu Leu Asn Ser Leu Thr Ser Glu Asp Ser Ala Val
                100                 105                 110

Tyr Tyr Cys Ser Arg Gly Gly Lys Thr Tyr Tyr Phe Asp Tyr Trp Gly
            115                 120                 125

Gln Gly Thr Thr Leu Thr Val Ser Pro Ala Lys Thr Thr Pro Pro Ser
        130                 135                 140

Val Tyr Pro Leu Ala Pro Gly Cys Gly Asp Thr Thr Gly Ser Ser Val
145                 150                 155                 160

Thr Leu Gly Cys Leu Val Lys Gly Tyr Phe Pro Glu Ser Val Thr Val
                165                 170                 175

Thr Trp Asn Ser Gly Ser Leu Ser Ser Val His Thr Phe Pro Ala
                180                 185                 190

Leu Leu Gln Ser Gly Leu Tyr Thr Met Ser Ser Val Thr Val Pro
            195                 200                 205

Ser Ser Thr Trp Pro Ser Gln Thr Val Thr Cys Ser Val Ala His Pro
        210                 215                 220

Ala Ser Thr Thr Val Asp Lys Lys Leu Glu Pro Ser Gly Pro Ile
225                 230                 235                 240

Ser Thr Ile Asn Pro Cys Pro Pro Cys Lys Glu Cys His Lys Cys Pro
                245                 250                 255

Ala Pro Asn Leu Glu Gly Gly Pro Ser Val Phe Ile Phe Pro Pro Asn
            260                 265                 270

Ile Lys Asp Val Leu Met Ile Ser Leu Thr Pro Lys Val Thr Cys Val
        275                 280                 285

Val Val Asp Val Ser Glu Asp Asp Pro Asp Val Arg Ile Ser Trp Phe
290                 295                 300

Val Asn Asn Val Glu Val His Thr Ala Gln Thr Gln Thr His Arg Glu
305                 310                 315                 320

Asp Tyr Asn Ser Thr Ile Arg Val Val Ser Ala Leu Pro Ile Gln His
                325                 330                 335

Gln Asp Trp Met Ser Gly Lys Glu Phe Lys Cys Lys Val Asn Asn Lys
            340                 345                 350

Asp Leu Pro Ser Pro Ile Glu Arg Thr Ile Ser Lys Ile Lys Gly Leu
        355                 360                 365

Val Arg Ala Pro Gln Val Tyr Ile Leu Pro Pro Ala Glu Gln Leu
370                 375                 380

Ser Arg Lys Asp Val Ser Leu Thr Cys Leu Val Val Gly Phe Asn Pro
385                 390                 395                 400

Gly Asp Ile Ser Val Glu Trp Thr Ser Asn Gly His Thr Glu Asn
            405                 410                 415

Tyr Lys Asp Thr Ala Pro Val Leu Asp Ser Asp Gly Ser Tyr Phe Ile
            420                 425                 430

Tyr Ser Lys Leu Asp Ile Lys Thr Ser Lys Trp Glu Lys Thr Asp Ser
            435                 440                 445

Phe Ser Cys Asn Val Arg His Glu Gly Leu Lys Asn Tyr Tyr Leu Lys
    450                 455                 460

Lys Thr Ile Ser Arg Ser Pro Gly Lys
465                 470

<210> SEQ ID NO 8
<211> LENGTH: 720
<212> TYPE: DNA
<213> ORGANISM: Artificial Sequence
<220> FEATURE:
<223> OTHER INFORMATION: 26A6 - Light chain

<400> SEQUENCE: 8

| | | |
|---|---|---|
| atgaagttgc ctgttaggct gttggtgctg atgttctgga ttcctgcttc cagcagtgat | 60 |
| gttgtgatga cccaaagtcc actctccctg cctgtcagtc ttggagatca agcctccatc | 120 |
| tcttgcagat ctagtcagag ccttgtacac agtaatggaa acacctattt acattggtac | 180 |
| ctgcagaagc caggccagtc tccaaagctc ctgatctaca agtttccaa ccgattttct | 240 |
| ggggtcccag acaggttcag tggcagtgga tcagggacag atttcacact caagatcaac | 300 |
| agagtggagg ctgaggatct gggagtttat ttctgctctc aaagtacaca tgttcctccg | 360 |
| gtcacgttcg gaggggggac caagctggaa ataaaacggg ctgatgctgc accaactgta | 420 |
| tccatcttcc caccatccag tgagcagtta acatctggag gtgcctcagt cgtgtgcttc | 480 |
| ttgaacaact ctaccccaa agacatcaat gtcaagtgga agattgatgg cagtgaacga | 540 |
| caaaatggcg tcctgaacag ttggactgat caggacagca agacagcac ctacagcatg | 600 |
| agcagcaccc tcacgttgac caaggacgag tatgaacgac ataacagcta cctgtgag | 660 |
| gccactcaca agacatcaac ttcacccatt gtcaagagct caacaggaa tgagtgttag | 720 |

<210> SEQ ID NO 9
<211> LENGTH: 239
<212> TYPE: PRT
<213> ORGANISM: Artificial Sequence
<220> FEATURE:
<223> OTHER INFORMATION: 26A6 - Light chain

<400> SEQUENCE: 9

Met Lys Leu Pro Val Arg Leu Leu Val Leu Met Phe Trp Ile Pro Ala
1               5                   10                  15

Ser Ser Ser Asp Val Val Met Thr Gln Ser Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Asn Arg Val Glu Ala Glu Asp Leu Gly Val Tyr Phe Cys

-continued

```
                100                 105                 110
Ser Gln Ser Thr His Val Pro Pro Val Thr Phe Gly Gly Gly Thr Lys
        115                 120                 125

Leu Glu Ile Lys Arg Ala Asp Ala Ala Pro Thr Val Ser Ile Phe Pro
        130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
                180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
        210                 215                 220

Thr Ser Thr Ser Pro Ile Val Lys Ser Phe Asn Arg Asn Glu Cys
225                 230                 235
```